(12) United States Patent
Von Teichert

(10) Patent No.: US 6,436,073 B1
(45) Date of Patent: Aug. 20, 2002

(54) BUTTERFLY ANCHOR FOR AN INFUSION SET

(76) Inventor: Joseph M. Von Teichert, 1020 N. Laurel Ave., Apt. #2, West Hollywood, CA (US) 90046-6029

( * ) Notice: Subject to any disclaimer, the term of this patent is extended or adjusted under 35 U.S.C. 154(b) by 65 days.

(21) Appl. No.: 09/636,086

(22) Filed: Aug. 9, 2000

Related U.S. Application Data

(63) Continuation of application No. 09/292,928, filed on Apr. 16, 1999.
(51) Int. Cl.[7] .................................................. A61M 5/32
(52) U.S. Cl. ................. 604/174; 604/180; 128/DIG. 26
(58) Field of Search ................................. 604/174, 177, 604/180, 158, 178, 179; 128/DIG. 26; 602/41–59

(56) References Cited

U.S. PATENT DOCUMENTS 5,735,272 A * 4/1998 Dillon et al. .......... 128/207.18

6,274,786 B1 * 8/2001 Heller .................... 128/888

* cited by examiner

Primary Examiner—Brian L. Casler
Assistant Examiner—Catherine Serke
(74) Attorney, Agent, or Firm—Belasco Jacobs & Townsley, LLP; David A. Belasco

(57) ABSTRACT

A butterfly anchor for an infusion set is described. The anchor provides a means to rapidly and securely stabilize an intravascular catheter for a patient while preventing the catheter from resting against or puncturing the vein wall subsequent to insertion or during later patient movement. The anchor includes a flexible anchor pad having an upper surface and a lower surface. The lower surface includes a means for attaching the anchor pad to the backing pad of a butterfly infusion set and to the skin of a patient. The anchor pad includes longitudinal reinforcing means located parallel to the long axis of the catheter and spaced apart from the center line of the anchor pad so as to control the orientation of the catheter in the patient's vein.

3 Claims, 1 Drawing Sheet

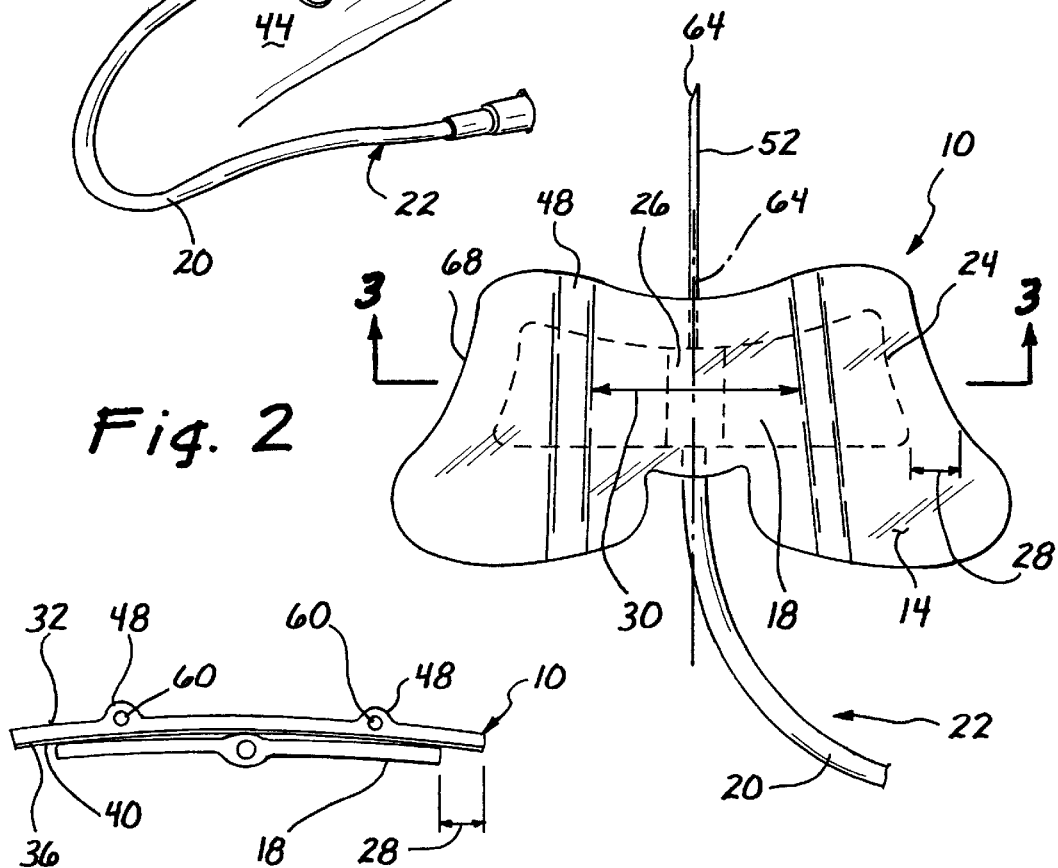

BUTTERFLY ANCHOR FOR AN INFUSION SET

REFERENCE

This application is a continuation of application Ser. No. 09/292,928, filed Apr. 16, 1999.

FIELD OF INVENTION

The invention pertains to medical devices and more particularly to devices for anchoring a catheter when inserted in the body so that the catheter does not rest against or puncture a vein wall.

BACKGROUND OF THE INVENTION

Infusion sets have been used in the medical world for many years to introduce and remove fluids from a patient's body. The set typically consists of a catheter or hollow needle mounted to a backing pad, a length of tubing connected at a first end to the catheter, and a connection fitting attached to a second end of the tubing. The catheter is inserted into a patient's vein and the backing pad is then secured to the patient's skin, usually with surgical tape. A supply of fluid to be infused into the patient is connected to the connection fitting and allowed to flow, by means of gravity, through the tubing, into the catheter and into the patient's vein.

If the backing pad is not properly secured to the patient's skin, the catheter may be dislodged. Further, if the angle at which the catheter is inserted into the patient's vein is not maintained, it is possible for the catheter to puncture a lower wall of the vein, preventing effective introduction of the infusion fluid into the patient's vein. A means of anchoring the catheter securely in place is needed to avoid dislodging or movement of the catheter by the patient.

The prior art includes a number of inventions directed towards stabilizing a catheter or needle inserted into a patient. U.S. Pat. No. 4,197,890 issued to Gordon et al in 1982 covers a winged fitting for use in intravascular needle or catheter insertion and subsequent stabilizing of the connection to the patient's skin. U.S. Pat. No. 5,156,641 issued to White et al. in 1992 provided for a naso-gastric catheter anchor system. The system employs a bilaterally symmetrical butterfly outline adhesive nose anchor. The anchor would affix a flexible small bore tubing to the nose.

U.S. Pat. No. 5,413,562 issued to Swauger in 1995 describes a stabilizing fitting for an intravenous catheter or syringe. The stabilizing fitting is anchored in place with velcro straps about the limb instead of a locally applied adhesive. Likewise, U.S. Pat. No. 5,449,349 issued to Sallee et al. in 1995 is directed towards an intravenous needle cover/protector. The catheter is housed within the device that is taped to the patient's skin.

U.S. Pat. No. 5,370,627 issued to Conway in 1994 illustrates a securing bridge for a catheter inserted directly into the umbilical stump of a neonate. The bridge includes a base onto which adhesive tape could be employed to secure the device to the neonate's skin.

Of a slightly different nature, U.S. Pat. No. 4,820,282 issued to Hogan in 1987 relates to a sheath for use in removing hypodermic needles from patients and retaining the point of the removed needle in the sheath when the needle and sheath are disposed of so as to protect against accidentally being pricked.

Of a very different nature is U.S. Pat. No. 4,898,587 issued to Mera in 1990. The Mera invention comprises a base plate, which includes a crotch, and a channel in its upper serface; and a cover. The base plate is designed to adhere on its underside to the patient's skin. The crotch is designed to fit around a catheter inserted into a vein and the tubing is retained in the channel with adhesive tape. The cover is then secured to the base plate for added protection.

It is an objective of the invention to provide a means to quickly and effectively attach a catheter and the backing pad of a butterfly infusion set to the skin of a patient. It is a further objective of the invention to stabilize and control the angle at which the catheter is maintained within the vein of a patient, so as to prevent accidental puncturing of the vein wall during subsequent infusion. It is yet a further objective of the invention to prevent the vein wall from being drawn into the catheter when the infusion set is used as a blood drawing device. It is still a further objective of the invention that the butterfly anchor is simple and inexpensive to manufacture.

SUMMARY OF THE INVENTION

A butterfly anchor for an infusion set may be constructed from the following components. A flexible catheter anchor pad sized and shaped to cover the backing pad of a butterfly infusion set. The anchor pad extends beyond the perimeter of the backing pad for a first predetermined distance. The first predetermined distance must be sufficient so that the anchor pad and backing pad do not lift during service. The anchor pad has a top surface and a bottom surface. The bottom surface includes a means for attachment to the skin of a patient and the backing pad. Reinforcing means are attached to the anchor pad, spaced apart from the center line of the anchor pad.

In use, when the backing pad of a butterfly infusion set is secured to the skin of a patient by the butterfly anchor, the reinforcing means will prevent the catheter of the infusion set from resting against or puncturing the vein wall during subsequent patient movement.

In a variant of the invention, the means for attachment is an adhesive located on the bottom surface of the anchor pad.

In another variant of the invention, the reinforcing means includes at least one rigid longitudinal element affixed to the anchor pad. The longitudinal element is oriented so as to be parallel to a long axis of the catheter when the anchor pad is attached to the backing pad of an infusion set.

DESCRIPTION OF THE DRAWINGS

FIG. 1 is a perspective view of the butterfly anchor and an infusion set;

FIG. 2 is a plan view of the butterfly anchor;

FIG. 3 is a cross sectional view of the butterfly anchor, illustrating the reinforcing means; and FIG. 4 is a cross-sectional view of the FIG. 1 embodiment illustrating the control of the catheter in the vein of a patient.

DETAILED DESCRIPTION OF THE PREFERRED EMBODIMENT

A butterfly anchor 10 for an infusion set, as illustrated in FIGS. 1–3, may be constructed from the following components. A flexible anchor pad 14 sized and shaped to cover the backing pad 18 of a butterfly infusion set 22. The anchor pad 14 extends beyond the perimeter 24 of the backing pad 18 for a first predetermined distance 28 so that it also overlays small portion of the catheter 52 and the joint 26 between the catheter 52 and the tube 20. The first predetermined distance 28 is large enough to prevent lifting of the anchor pad 14 and backing pad 18 during service. The anchor pad 14 has a top surface 32 and a bottom surface 36. The bottom surface 36 includes a means 40 for attachment to the skin 44 of a patient and the backing pad 18. Reinforcing means 48 are attached to the anchor pad 14 approximately equidistant between the center line 64 and the edge 68 of the anchor pad 14. The reinforcing means 48 define between them a center section 30 of the backing pad 18 and the butterfly infusion set 22.

As illustrated in FIGS. 3 and 4, when the backing pad 18 of a butterfly infusion set 22 is secured to the skin 44 of a patient by the butterfly anchor 10, the reinforcing means 48 will prevent the catheter 52 of the infusion set 22 from resting against or puncturing the vein wall 56 during subsequent patient movement.

In a variant of the invention, the means 40 for attachment is an adhesive located on the bottom surface 36 of the anchor pad 14.

In another variant of the invention, the reinforcing means 48 includes at least one rigid longitudinal element 60 affixed to the anchor pad 14. The longitudinal element 60 is oriented so as to be parallel to a long axis 64 of the catheter 52 when the anchor pad 14 is attached to the backing pad 18 of an infusion set 22. The reinforcing element 60 may be made of metal.

It will be apparent to those most familiar with the art to which this invention pertains that this invention 10 differs considerably from the Mera invention discussed above. Mera intended for the tube to overlie and be attached to the top surface of his base plate and the catheter to pass through the crotch. In the instant invention 10, the anchor pad 14 is designed to cover and retain in place the backing pad 18 and the joint 26, as well as the portions. of the tube 20 and catheter 52 of a butterfly infusion set 22. The raised portions of Mera's invention are designed to form a channel for securing the tube and are thus close together and not intended for reinforcement. In the instant invention 10, the reinforcing means 48, 60 are not intended to form a channel and are spaced apart in order to properly retain the catheter 52 in proper position. Lastly, there is no relationship between size of the Mera invention and the size of the backing pad 18 of a butterfly infusion set 22. This is because the Mera invention is intended as an alternate to a butterfly infusion set 22. The Mera invention is not intended to be used in conjunction with a butterfly infusion set 22. In sharp contrast, the instant invention 10 is definitely intended to be used in conjunction with a butterfly infusion set 22. Consequently, the anchor pad 14 of the instant invention must be larger than the backing pad 18 of the standard butterfly infusion set 22 in all dimensions, as is explained above and illustrated in the Figures.

The following reference numerals are used in FIGS. 1–4:

10 Butterfly anchor
14 Flexible anchor pad
18 Backing pad
20 Tube
22 Butterfly infusion set
24 Perimeter of backing pad
26 Joint between tube and catheter
28 First predetermined distance
30 Center section
32 Top surface of anchor pad
36 Bottom surface of anchor pad
40 Means for attachment to the skin
44 Skin of patient
48 Reinforcing means
52 Catheter
56 Vein wall
60 Rigid, longitudinal member
64 Long axis of catheter, long axis of anchor pad, and center line of anchor pad The butterfly anchor for an infusion set 10 has been described with reference to particular embodiments. Other modifications and enhancements can be made without departing from the spirit and scope of the claims that follow.

What is claimed is:

1. A butterfly anchor for an infusion set comprising:

a flexible anchor pad having a center line; said flexible anchor pad sized and shaped to cover a backing pad of a butterfly infusion set and to extend beyond a perimeter of said backing pad for a first predetermined distance; said flexible anchor pad having a top surface and a bottom surface, said bottom surface including a means for attachment to the skin of a patient and said backing pad; said flexible anchor pad being flexible enough to contour closely over a joint between a catheter and a tube of a butterfly infusion set; and rigid reinforcing means embedded within said top surface of, parallel to the long axis of, and spaced apart from the center line of said flexible anchor pad with a spacing sufficient to accommodate a center section of a butterfly infusion set backing pad;

whereby, when the backing pad of a butterfly infusion set is secured to the skin of a patient by the butterfly anchor, said flexible anchor pad will contour closely over said joint and will prevent a catheter from resting against or puncturing the vein wall during subsequent patient movement.

2. A butterfly anchor for an infusion set as described in claim 1 wherein said means for attachment is an adhesive disposed on said bottom surface.

3. A butterfly anchor for an infusion set as described in claim 1 in which said rigid reinforcing means includes a metallic element encapsulated within said flexible anchor pad.

* * * * *